(12) United States Patent
Augarten et al.

(10) Patent No.: US 9,211,207 B2
(45) Date of Patent: Dec. 15, 2015

(54) POWER REGULATED IMPLANT

(75) Inventors: Mike Augarten, Goleta, CA (US); Sean Snow, Carpinteria, CA (US)

(73) Assignee: APOLLO ENDOSURGERY, INC., Austin, TX (US)

(*) Notice: Subject to any disclaimer, the term of this patent is extended or adjusted under 35 U.S.C. 154(b) by 1243 days.

(21) Appl. No.: 12/859,196

(22) Filed: Aug. 18, 2010

(65) Prior Publication Data

US 2012/0046674 A1 Feb. 23, 2012

(51) Int. Cl.
*F04B 49/02* (2006.01)
*A61F 5/00* (2006.01)
*F04B 49/06* (2006.01)

(52) U.S. Cl.
CPC .......... *A61F 5/0059* (2013.01); *F04B 49/022* (2013.01); *F04B 49/06* (2013.01); *A61F 2005/0016* (2013.01); *F04B 2201/0801* (2013.01)

(58) Field of Classification Search
CPC ... A61F 5/0053; A61F 5/0066; A61F 5/0059; F04B 49/02; F04B 49/06; F04B 49/022; F04B 17/003; F04B 2203/0202; F04B 2201/0801; F04B 2205/06
USPC ............... 417/32, 44.1, 413.2, 45, 44.11; 310/317; 600/37, 561; 604/891.1
See application file for complete search history.

(56) References Cited

U.S. PATENT DOCUMENTS

| | | | |
|---|---|---|---|
| 2,163,048 A | 6/1939 | McKee | |
| 3,667,081 A | 6/1972 | Burger | |
| 3,840,018 A | 10/1974 | Heifetz | |
| 4,118,805 A | 10/1978 | Reimels | |
| 4,157,713 A | 6/1979 | Clarey | |
| 4,340,083 A | 7/1982 | Cummins | |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Corno et al.; "A new implantable device for telemetric control of pulmonary blood flow," New Ideas; received Apr. 24, 2004; received in revised form Jul. 12, 2002; accepted Jul. 22, 2002.

(Continued)

*Primary Examiner* — Devon Kramer
*Assistant Examiner* — Nathan Zollinger
(74) *Attorney, Agent, or Firm* — Gordon & Jacobson, P.C.

(57) ABSTRACT

An implantable pumping system for pumping a fluid in an implantable gastric banding system comprises a pump for pumping the fluid. A voltage source provides a pump voltage to the system, and a voltage control circuit increases or decreases the pump voltage. A pump driver applies the pump voltage to the pump at a phase and a frequency. The implantable pumping system comprises a sensor that monitors a parameter to facilitate adjusting at least one of the phase or the frequency to maintain a desired value of the parameter. The parameter is associated with at least one of the implantable pumping system or the implantable gastric banding system. A micro controller is configured to manipulate at least one of the phase or the frequency to maintain the desired value of the parameter. The sensor may comprise a temperature sensor, a pressure sensor, and/or a flow rate sensor.

3 Claims, 2 Drawing Sheets

(56) References Cited

U.S. PATENT DOCUMENTS

| | | |
|---|---|---|
| 4,406,656 A | 9/1983 | Hattler et al. |
| 4,450,375 A | 5/1984 | Siegal |
| 4,592,339 A | 6/1986 | Kuzmak et al. |
| 4,592,355 A | 6/1986 | Antebi |
| 4,601,713 A | 7/1986 | Fuqua |
| 4,671,351 A | 6/1987 | Rappe |
| 4,696,288 A | 9/1987 | Kuzmak et al. |
| 4,743,789 A | 5/1988 | Puskas |
| 4,760,837 A | 8/1988 | Petit |
| 4,881,939 A | 11/1989 | Newman |
| 4,883,467 A | 11/1989 | Franetzki et al. |
| 4,944,659 A | 7/1990 | Labbe |
| 5,045,060 A | 9/1991 | Melsky et al. |
| 5,074,868 A | 12/1991 | Kuzmak |
| 5,089,019 A | 2/1992 | Grandjean |
| 5,120,313 A | 6/1992 | Elftman |
| 5,160,338 A | 11/1992 | Vincent |
| 5,226,429 A | 7/1993 | Kuzmak |
| 5,259,399 A | 11/1993 | Brown |
| 5,326,349 A | 7/1994 | Baraff |
| 5,343,894 A | 9/1994 | Frisch et al. |
| 5,360,445 A | 11/1994 | Goldowsky |
| 5,449,368 A | 9/1995 | Kuzmak |
| 5,458,568 A | 10/1995 | Racchini et al. |
| 5,496,312 A | 3/1996 | Klicek |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,658,298 A | 8/1997 | Vincent et al. |
| 5,676,162 A | 10/1997 | Larson, Jr. et al. |
| 5,733,257 A | 3/1998 | Sternby |
| 5,748,200 A | 5/1998 | Funahashi |
| 5,759,015 A | 6/1998 | Van Lintel et al. |
| 5,766,232 A | 6/1998 | Grevious et al. |
| 5,779,911 A * | 7/1998 | Haug et al. .................... 210/739 |
| 5,807,311 A | 9/1998 | Palestrant |
| 5,861,014 A | 1/1999 | Familoni |
| RE36,176 E | 3/1999 | Kuzmak |
| 5,910,149 A | 6/1999 | Kuzmak |
| 5,938,669 A | 8/1999 | Klaiber et al. |
| 6,024,340 A | 2/2000 | Lazarus et al. |
| 6,024,704 A | 2/2000 | Meador et al. |
| 6,042,345 A | 3/2000 | Bishop et al. |
| 6,067,991 A | 5/2000 | Forsell |
| 6,074,341 A | 6/2000 | Anderson et al. |
| 6,083,249 A | 7/2000 | Familoni |
| 6,102,678 A | 8/2000 | Peclat |
| 6,102,922 A | 8/2000 | Jakobsson et al. |
| 6,164,933 A | 12/2000 | Tani et al. |
| 6,210,347 B1 | 4/2001 | Forsell |
| 6,221,024 B1 | 4/2001 | Miesel |
| 6,306,088 B1 | 10/2001 | Krausman et al. |
| 6,327,503 B1 | 12/2001 | Familoni |
| 6,417,750 B1 | 7/2002 | Sohn |
| 6,432,040 B1 | 8/2002 | Meah |
| 6,439,539 B1 | 8/2002 | Powell |
| 6,450,173 B1 | 9/2002 | Forsell |
| 6,450,946 B1 | 9/2002 | Forsell |
| 6,450,987 B1 | 9/2002 | Kramer |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,475,136 B1 | 11/2002 | Forsell |
| 6,511,490 B2 | 1/2003 | Robert |
| 6,527,701 B1 | 3/2003 | Sayet et al. |
| 6,547,801 B1 | 4/2003 | Dargent et al. |
| 6,579,301 B1 | 6/2003 | Bales et al. |
| 6,676,674 B1 | 1/2004 | Dudai |
| 6,681,135 B1 | 1/2004 | Davis et al. |
| 6,685,668 B1 | 2/2004 | Cho et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,940,467 B2 | 9/2005 | Fisher et al. |
| 6,966,875 B1 | 11/2005 | Longobardi |
| 7,017,583 B2 | 3/2006 | Forsell |
| 7,017,883 B2 | 3/2006 | Bayer et al. |
| 7,019,436 B2 | 3/2006 | Rueger |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,048,519 B2 | 5/2006 | Fong et al. |
| 7,058,434 B2 | 6/2006 | Wang et al. |
| 7,060,080 B2 | 6/2006 | Bachmann |
| 7,066,486 B2 | 6/2006 | Birk |
| 7,118,526 B2 | 10/2006 | Egle |
| 7,128,750 B1 | 10/2006 | Stergiopulos |
| 7,191,007 B2 | 3/2007 | Desai et al. |
| 7,198,250 B2 | 4/2007 | East |
| 7,204,821 B1 | 4/2007 | Clare et al. |
| 7,206,637 B2 | 4/2007 | Salo |
| 7,238,191 B2 | 7/2007 | Bachmann |
| 7,282,023 B2 | 10/2007 | Frering |
| 7,284,966 B2 | 10/2007 | Xu et al. |
| 7,288,064 B2 | 10/2007 | Boustani et al. |
| 7,310,557 B2 | 12/2007 | Maschino et al. |
| 7,311,503 B2 | 12/2007 | Van Lintel et al. |
| 7,311,716 B2 | 12/2007 | Byrum |
| 7,311,717 B2 | 12/2007 | Egle |
| 7,314,443 B2 | 1/2008 | Jordan et al. |
| 7,338,433 B2 | 3/2008 | Coe |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,366,571 B2 | 4/2008 | Armstrong |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,481,763 B2 | 1/2009 | Hassler et al. |
| 7,500,944 B2 | 3/2009 | Byrum et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,699,770 B2 | 4/2010 | Hassler, Jr. et al. |
| 7,727,141 B2 | 6/2010 | Hassler, Jr. et al. |
| 7,758,493 B2 | 7/2010 | Gingras |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,794,386 B2 | 9/2010 | Brooks |
| 7,811,298 B2 | 10/2010 | Birk |
| 7,844,342 B2 | 11/2010 | Dlugos et al. |
| 7,908,493 B2 * | 3/2011 | Bieswanger et al. .......... 713/300 |
| 8,308,630 B2 * | 11/2012 | Birk et al. ........................ 600/37 |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0139208 A1 | 10/2002 | Yatskov |
| 2002/0193679 A1 | 12/2002 | Malave et al. |

(56) References Cited

U.S. PATENT DOCUMENTS

| | | |
|---|---|---|
| 2002/0198548 A1 | 12/2002 | Robert |
| 2003/0019498 A1 | 1/2003 | Forsell |
| 2003/0045775 A1 | 3/2003 | Forsell |
| 2003/0055311 A1 | 3/2003 | Neukermans et al. |
| 2003/0066536 A1 | 4/2003 | Forsell |
| 2003/0073880 A1 | 4/2003 | Polsky et al. |
| 2003/0158569 A1 | 8/2003 | Wazne |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0059393 A1 | 3/2004 | Policker et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0143765 A1 | 6/2005 | Bachmann et al. |
| 2005/0143766 A1 | 6/2005 | Bachmann et al. |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0216042 A1 | 9/2005 | Gertner |
| 2005/0225202 A1* | 10/2005 | Vogeley et al. ............... 310/317 |
| 2005/0228415 A1 | 10/2005 | Gertner |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler et al. |
| 2005/0267533 A1 | 12/2005 | Gertner |
| 2005/0277899 A1 | 12/2005 | Conlon et al. |
| 2005/0283041 A1 | 12/2005 | Egle |
| 2005/0288739 A1 | 12/2005 | Hassler |
| 2005/0288740 A1 | 12/2005 | Hassler |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0161186 A1 | 7/2006 | Hassler, Jr. et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0195139 A1 | 8/2006 | Gertner |
| 2006/0197412 A1 | 9/2006 | Rasmussen |
| 2006/0199997 A1 | 9/2006 | Hassler et al. |
| 2006/0204367 A1* | 9/2006 | Meza et al. ............... 417/53 |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212053 A1 | 9/2006 | Gertner |
| 2006/0235448 A1 | 10/2006 | Roslin et al. |
| 2006/0247722 A1 | 11/2006 | Maschino et al. |
| 2006/0247724 A1 | 11/2006 | Gerber et al. |
| 2006/0252982 A1 | 11/2006 | Hassler, Jr. et al. |
| 2006/0264699 A1 | 11/2006 | Gertner |
| 2006/0276812 A1 | 12/2006 | Hill et al. |
| 2007/0015954 A1 | 1/2007 | Dlugos |
| 2007/0015955 A1 | 1/2007 | Tsonton |
| 2007/0016262 A1 | 1/2007 | Gross et al. |
| 2007/0027356 A1 | 2/2007 | Ortiz |
| 2007/0078476 A1 | 4/2007 | Hull et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0185462 A1 | 8/2007 | Byrum |
| 2007/0218083 A1 | 9/2007 | Brooks |
| 2007/0232848 A1 | 10/2007 | Forsell |
| 2007/0235083 A1 | 10/2007 | Dlugos |
| 2007/0250085 A1 | 10/2007 | Bachmann et al. |
| 2007/0250086 A1 | 10/2007 | Wiley et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2008/0009680 A1 | 1/2008 | Hassler, Jr. |
| 2008/0015406 A1 | 1/2008 | Dlugos et al. |
| 2008/0027469 A1 | 1/2008 | Bachmann |
| 2008/0097496 A1 | 4/2008 | Chang et al. |
| 2008/0108862 A1 | 5/2008 | Jordan et al. |
| 2008/0166028 A1 | 7/2008 | Turek et al. |
| 2008/0177224 A1* | 7/2008 | Kelly et al. ............... 604/74 |
| 2008/0221598 A1 | 9/2008 | Dlugos et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0319435 A1 | 12/2008 | Rioux et al. |
| 2008/0319544 A1* | 12/2008 | Yaegashi ............... 623/3.28 |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1* | 8/2009 | Ortiz et al. ............... 606/157 |
| 2009/0204132 A1 | 8/2009 | Ortiz et al. |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1 | 8/2009 | Coe et al. |
| 2009/0222031 A1 | 9/2009 | Axelsson |
| 2009/0222065 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2009/0312785 A1 | 12/2009 | Stone et al. |

(56) References Cited

U.S. PATENT DOCUMENTS

| | | | |
|---|---|---|---|
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0152532 A1 | 6/2010 | Marcotte |
| 2010/0185049 A1 | 7/2010 | Birk et al. |
| 2010/0191271 A1 | 7/2010 | Lau et al. |
| 2010/0228080 A1 | 9/2010 | Tavori et al. |
| 2010/0249803 A1 | 9/2010 | Griffiths |
| 2010/0280310 A1 | 11/2010 | Raven |
| 2010/0305397 A1 | 12/2010 | Birk et al. |
| 2010/0324358 A1 | 12/2010 | Birk et al. |
| 2010/0324359 A1 | 12/2010 | Birk |
| 2011/0034760 A1* | 2/2011 | Brynelsen et al. ............... 600/37 |

FOREIGN PATENT DOCUMENTS

| | | |
|---|---|---|
| DE | 4225524 | 2/1994 |
| DE | 10020688 | 12/2000 |
| EP | 0119596 | 9/1984 |
| EP | 0230747 | 8/1987 |
| EP | 0611561 | 8/1994 |
| EP | 0695558 | 2/1996 |
| EP | 0867808 | 11/1998 |
| EP | 1072282 | 1/2001 |
| EP | 1396242 | 3/2004 |
| EP | 1396243 | 3/2004 |
| EP | 1491167 | 12/2004 |
| EP | 1547549 | 6/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 2074970 | 7/2009 |
| EP | 2074971 | 7/2009 |
| EP | 2087862 | 8/2009 |
| EP | 2095796 | 9/2009 |
| EP | 2095798 | 9/2009 |
| FR | 2797181 | 2/2001 |
| FR | 2823663 | 10/2002 |
| FR | 2855744 | 12/2004 |
| FR | 2921822 | 4/2009 |
| JP | 2005-334658 | 12/2005 |
| WO | WO 89/11701 | 11/1989 |
| WO | WO 00/09047 | 2/2000 |
| WO | WO 00/09048 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 2001/70131 | 9/2001 |
| WO | WO 02/26317 | 4/2002 |
| WO | WO 02/053093 | 7/2002 |
| WO | WO 02/065948 | 8/2002 |
| WO | WO 03/077191 | 9/2003 |
| WO | WO 03/105732 | 12/2003 |
| WO | WO 2004/014245 | 2/2004 |
| WO | WO 2004/019671 | 3/2004 |
| WO | WO 2005/007232 | 1/2005 |
| WO | WO 2005/009305 | 2/2005 |
| WO | WO 2005/087147 | 9/2005 |
| WO | WO 2005/094447 | 10/2005 |
| WO | WO 2006/083885 | 8/2006 |
| WO | WO 2006/108203 | 10/2006 |
| WO | WO 2008/109300 | 9/2008 |
| WO | WO 2009/132127 | 10/2009 |

OTHER PUBLICATIONS

"Innovative medical devices and implants," LGSP Medical futures, p. 5.

Corno et al.; "FloWatchTM in clipped and inclipped position," Interact Cardio Vase Thorac Surg 2002; 1:46-49.

BioEnterics Lap-Band Adjustable Gastric Banding System, Inamed Health, pub. Aug. 28, 2003 pp. 1-115.

Iverson et al.; "Recent Advances in Microscale Pumping Technologies: A Review and Evaluation"; Microfluid Nanofluid; vol. 5; pp. 145-174; Feb. 19, 2008.

* cited by examiner

POWER REGULATED IMPLANT

FIELD

The present invention generally relates to medical systems and apparatus and uses thereof for treating obesity and/or obesity-related diseases, and more specifically, relates to systems and methods for regulating power supplied to the medical systems and apparatus.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, the food held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Non-invasive adjustment systems and methods have also been proposed to change the constriction of a gastric band, for example, without the use of a hypodermic needle. Some of these systems utilize implantable pumps to perform the constriction changes. However, the system specifications for these pumps, such as small size, power dissipation, flow rate, back pressure, and magnetic resonance imaging, result in challenging constraints for pump implementation.

Furthermore, some non-invasive systems that utilize pumps may generate excessive heat, such that tissue surrounding the implanted device may be heated more than is desirable. The amount of power utilized to drive the pump may contribute to the excess heating.

Additionally, some body-related systems utilize temperature measurements. For example, Grandjean, U.S. Pat. No. 5,089,019, generally discloses a muscle work output monitor that uses intramuscular temperature variation measurements. However, Grandjean does not disclose controlling operation of an implantable device based on the temperature associated with the implantable device.

Klicek, U.S. Pat. No. 5,496,312, generally discloses a control that responds to impedance and temperature between active and return electrodes of an electrosurgical generator during tissue desiccation. However, Klicek does not disclose utilizing temperature measurements to regulate the fluid flow and/or pressure within an implantable device.

Davis, et al., U.S. Pat. No. 6,681,135, generally discloses a pacemaker that is operational based on temperature. Similarly, Salo, U.S. Pat. No. 7,206,637, discloses cardiac pacing using sensed coronary vein blood temperature. And Armstrong, U.S. Pat. No. 7,366,571, discloses a neurostimulator with activation based on changes in body temperature. But Davis, Salo, and Armstrong do not disclose determining and/or inferring a temperature of an implantable component to control operation of an implantable gastric band.

Thus, there continues to remain a need for more effective implantable pump systems for use with adjustable gastric bands, particularly such implantable pump systems with pumping capability that achieves the desired flow rate within other design parameters such as voltage and temperature.

Further, there is a need for more effective implantable pump systems for adjustable gastric bands that are more efficient and are capable of monitoring various implantable system parameters in order to achieve a higher operational efficiency and to ensure operation within desired parameters.

SUMMARY

Generally described herein are implantable pumping systems for implantable gastric banding systems. The apparatus and systems described herein aid in facilitating obesity control and/or treating obesity-related diseases while being non-invasive once implanted.

In one embodiment, an implantable pumping system for pumping a fluid in an implantable gastric banding system comprises a pump for pumping the fluid. A voltage source provides a pump voltage to the system, and a voltage control circuit increases or decreases the pump voltage. A pump driver applies the pump voltage to the pump at a desired and/or proper phase and frequency.

Further, in an embodiment, the implantable pumping system comprises a sensor that monitors a parameter to facilitate adjusting at least one of the phase, the pump voltage, or the frequency to maintain a desired value of the parameter. The parameter is associated with at least one of the implantable pumping system or the implantable gastric banding system. A micro controller is configured to manipulate at least one of the phase or the frequency to maintain the desired value of the parameter.

In one embodiment, the pump comprises a piezo actuator. In another embodiment, the pump is an electro-mechanical pump. For example, the pump may comprise a stepper motor.

In various embodiments, the sensor may comprise a temperature sensor, a pressure sensor, and/or a flow rate sensor. Where the measured parameter is temperature, the temperature may be associated with at least one of the pump, an enclosure for the implantable pumping system, the micro controller, or a radio transmitter. The measured temperature may be correlated to a temperature of the enclosure for the implantable pumping system in an embodiment where the temperature of the enclosure is a temperature of interest.

Further, in accordance with an embodiment, a method for monitoring a parameter of an implantable pumping system for an implantable gastric banding system comprises setting a frequency and/or a voltage of a power consumed by a pump. The method further comprises measuring the parameter, wherein the parameter is associated with the power consumed by the pump. The measured parameter is compared to a desired threshold. If the measured parameter is outside of the desired threshold, at least one of a frequency or a voltage may be adjusted to modify operation of the pump and bring the parameter back within the desired threshold. The measurement of the parameter is periodically repeated. In various embodiments, the measured parameter may be at least one of temperature, flow rate, or pressure. Additionally, the parameter may comprise a temperature change with respect to a calibrated temperature of the implantable pumping system.

In an embodiment, the method further comprises scaling the frequency utilizing at least one of software or hardware, and/or scaling the voltage utilizing at least one of software or hardware. Further, setting the frequency and the voltage may comprise setting a maximum frequency and a maximum voltage. In an embodiment, the method further comprises cycling the pump on or off when the parameter is above or below the desired threshold. The frequency and the voltage are reset up to the maximum frequency and/or up to the maximum voltage when the parameter is below the desired threshold.

DETAILED DESCRIPTION

The present invention generally provides remotely adjustable gastric banding systems, for example, for treatment of obesity and obesity related conditions, as well as systems for controlling inflation of gastric banding systems.

A remotely adjustable gastric band is a medical device which allows a healthcare worker to adjust a gastric band without utilizing hypodermic needles to connect to an implanted access port. An external, handheld controller may be used to send radio frequency signals for powering and communicating with the implanted device. The implanted device may fill or drain the gastric band as requested by the healthcare worker via the handheld controller. The handheld controller may be a remote device configured to produce a telemetric signal that controls the various components of the gastric banding system.

In various embodiments of the present invention, the filling and draining of the band is accomplished by a set of fluidic elements including pumps, valves, and sensors which monitor and/or move fluid between the gastric band and a reservoir. In accordance with various embodiments, different numbers, types, and orientations of the fluidic elements may be utilized to obtain the desired results. Any and/or all of these various components may be configured to be controlled by a remote transmitter, such as a handheld controller.

For example, an implantable pump may be utilized to move the fluid through the adjustable gastric banding system. Considerations involved with the implantable pump include size, power dissipation, flow rate, back pressure, and effects on magnetic resonance imaging. Various embodiments of the present invention provide adjustable gastric banding systems that achieve the appropriate specifications for these and other considerations.

Figure 1:
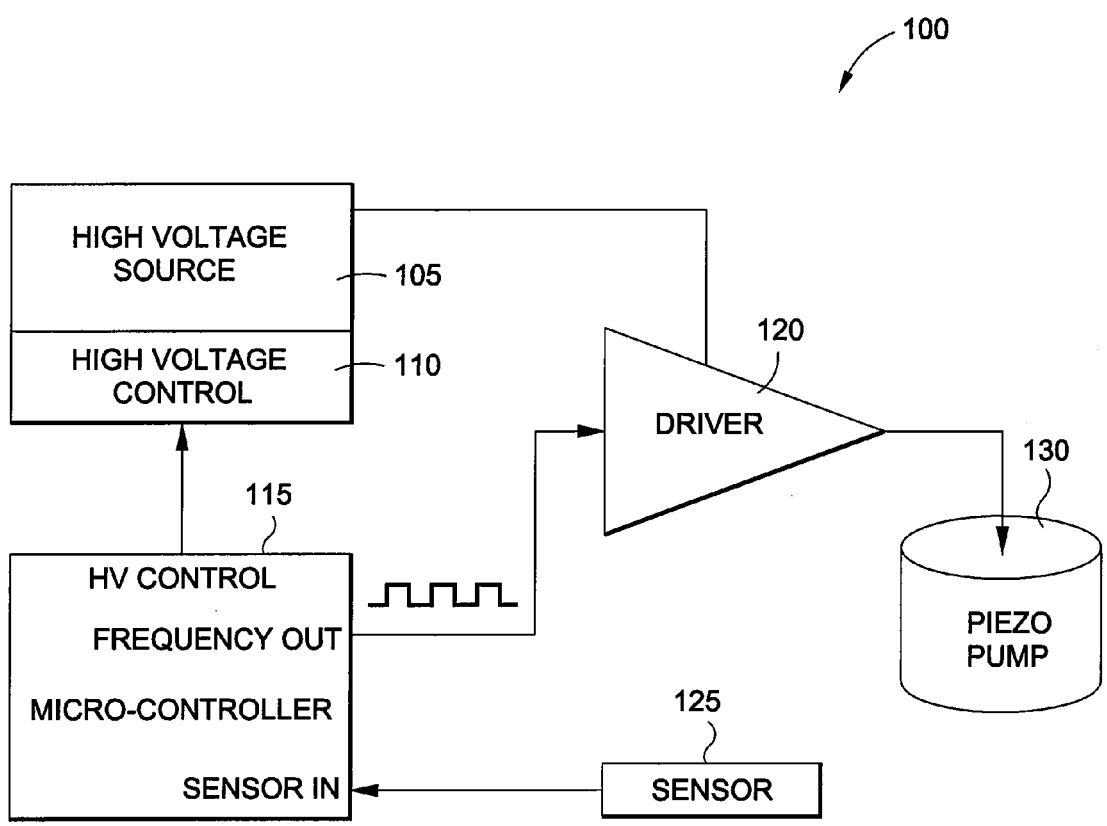
FIG. 1 illustrates a schematic view of an implantable pumping system according to an embodiment of the present invention.

Turning now to FIG. 1, an implantable pumping system 100, according to an embodiment, comprises a piezo actuator based pump 130. A voltage source, such as a high voltage source 105 is utilized to polarize the piezo actuators in the pump 130. A voltage control circuit, such as a high voltage control circuit 110 is configured to increase or decrease the magnitude of the voltage. In various embodiments, the voltage may be in the range of approximately 20 volts to approximately 300 volts.

A pump driver 120 is configured to apply the pump voltage to the pump 130 with a proper phase and frequency. In various embodiments, the frequency may be in the range of approximately 10 Hz to approximately 1000 Hz. Further, in various embodiments, the voltage applied to the pump 130 by the driver 120 may be in the range of approximately 20 volts to approximately 300 volts. Additionally, in various embodiments, the pump pressure may be in the range of approximately 0.1 psi to approximately 20 psi, and the pump rate may be in the range of approximately 0.1 mL per minute to approximately 10 mL per minute.

A sensor 125 is configured to monitor various parameters related to power, as will be discussed further below. Additionally, a micro controller 115 is configured to manipulate the various power control parameters. In other embodiments, components in the implantable pumping system 100 may be utilized in conjunction with other types of pumps, such as electro-mechanical pumps, including pumps with stepper motors, but the voltages and frequencies may be different depending on the design of the systems.

As the pump 130 operates to fill or drain the inflatable portion of the gastric band, it generates heat. When the change in inflation (or a volume change in the inflatable portion) is large enough, the pump 130 and/or other components of the implantable pumping system 100 can exceed desired temperatures. For example, the implantable pumping system 100 may be disposed within an enclosure, and the surface of the enclosure, which is in contact with the tissue of a patient, may exceed regulatory temperature limits.

In accordance with an embodiment of the present invention, the power consumed by the implantable pumping system 100 may be controlled in order to maintain the temperature associated with the system 100 within regulatory and/or other limits. By monitoring power-related parameter(s) associated with the system 100 it is possible to provide feedback to the system 100 in order to modify operation of the system 100 and maintain the temperature within desired limits. In an embodiment, the circuits for monitoring and control of the temperature and/or other parameters are within an implantable portion of the implantable pumping system 100 to allow for a faster response.

The power consumed by the pump 130 may be determined by the following:

$$\text{Power} = CV^2F \tag{1}$$

where "C" represents the capacitance of the piezo elements of the pump 130, "V" represents the overall voltage applied to the piezo elements, and "F" represents the frequency at which the piezo elements are switched. In various embodiments, to achieve a desired performance of the pump 130, the voltage is set near the maximal end of its range, and the frequency is optimized for pressure and flow maximums within the implantable system 100. The capacitance is determined by the physical dimensions and/or material properties of the piezo actuators.

In various embodiments, the pump 130 and the associated circuitry and components consume a majority of the power in the implantable pumping system 100. In various embodiments, the power consumed is in the range of approximately 50 mW to approximately 1000 mW. Accordingly, it is desirable to reduce and/or modify the amount of power consumed by the pump 130 and related circuits. By monitoring a power-related parameter associated with the system 100 and/or the pump 130, the pump 130 voltage and/or frequency may be modified or controlled to achieve a desired amount of power consumed.

Scaling the frequency of the piezo pump 130 may be implemented in software and/or hardware, and thus is relatively simple. In various embodiments, scaling the frequency may be accomplished utilizing software and/or hardware. Scaling the voltage may be more involved because it may include hardware and/or software modifications, for example, to change the pump voltages driving the piezo actuators. However, controlling the voltage may be more advantageous since power is a squared function of voltage, as indicated in (1) above.

Various parameters related to the implantable system 100 may be monitored in order to control operation of the pump 130. For example, pressure may be monitored (e.g., in the inflatable portion of the gastric band), and the voltage and/or frequency may be adjusted as needed to obtain desired operation of the system 100. As pressure increases, more power is consumed by the system 100 in order to continue increasing the pressure, and the voltage and/or frequency may be increased only as needed to avoid overheating of the system 100. Further, flow rate within the system 100 may be monitored so that as the flow rate decreases, the voltage and/or frequency may be increased only as needed.

In various embodiments, temperature of the system 100 may be monitored, and the voltage and/or frequency may be adjusted in order to maintain the system 100 temperature within the desired operating parameters. In one embodiment, the temperature is a targeted operational parameter, and the pressure and flow rate are indirect measures of the system 100 temperature. For example, as the volume of fluid in the inflatable portion of the gastric band increases, the pressure in the inflatable portion increases, and the pump 130 is pumping against this increased pressure. As a result, more power is needed by the pump 130 in order to continue pumping the fluid. More power may be achieved by higher voltage and/or higher frequency utilized by the pump 130. Thus, measuring pressure and/or flow rate provides an indirect indication of temperature, but monitoring temperature directly may provide a more accurate indication of how the system 100 is operating. For example, temperature may be monitored to determine that the temperature is within a desirable threshold. In an embodiment, this temperature threshold is related to the temperature of the enclosure for the implantable pumping system.

Further, using pressure and/or flow rate to indicate temperature may result in less-efficient operation of system 100. For instance, monitoring these parameters may result in the system starting at its lowest performance and ramping to higher performance as needed. In other words, performance may be sub-optimal in cases where the piezo pump does not generate heat above a predetermined threshold. Therefore, in an embodiment, temperature is monitored to enhance the operation of the system 100, and performance is reduced in order to maintain temperature within the desired parameters.

In an embodiment, performance of the system 100 may be increased while monitoring the pressure and/or flow rate. For example, the system 100 may begin operation approximately at a maximum performance (e.g., at a determined voltage and/or frequency), and then the pump 130 may be shut off once a predetermined measurement threshold for pressure and/or flow rate is met. This predetermined measurement threshold may be advantageously determined to keep the temperature of the system 100 within the desired operating parameters. Then, when the pressure and/or flow rate changes from the measurement threshold, the pump 130 may again be switched on up to a maximum performance setting, and the pump 130 is effectively cycled on and off to control temperature of the system 100. Further, in an embodiment, above a predetermined threshold for pressure, and/or below a predetermined threshold for flow rate, the pump 130 may be cycled on and off until a target pressure and/or flow rate is achieved. Such cycling facilitates controlling the temperature of the system, for example, the temperature of the enclosure for the system.

In accordance with various embodiments, the parameters being measured may be measured continuously to determine appropriate control of the system 100, and the system 100 may similarly be controlled continuously. In another embodiment, the monitored variables (e.g., pressure, flow rate, temperature etc.) may be sampled, and the feedback may be applied, in discrete steps and/or at discrete intervals.

Figure 2:
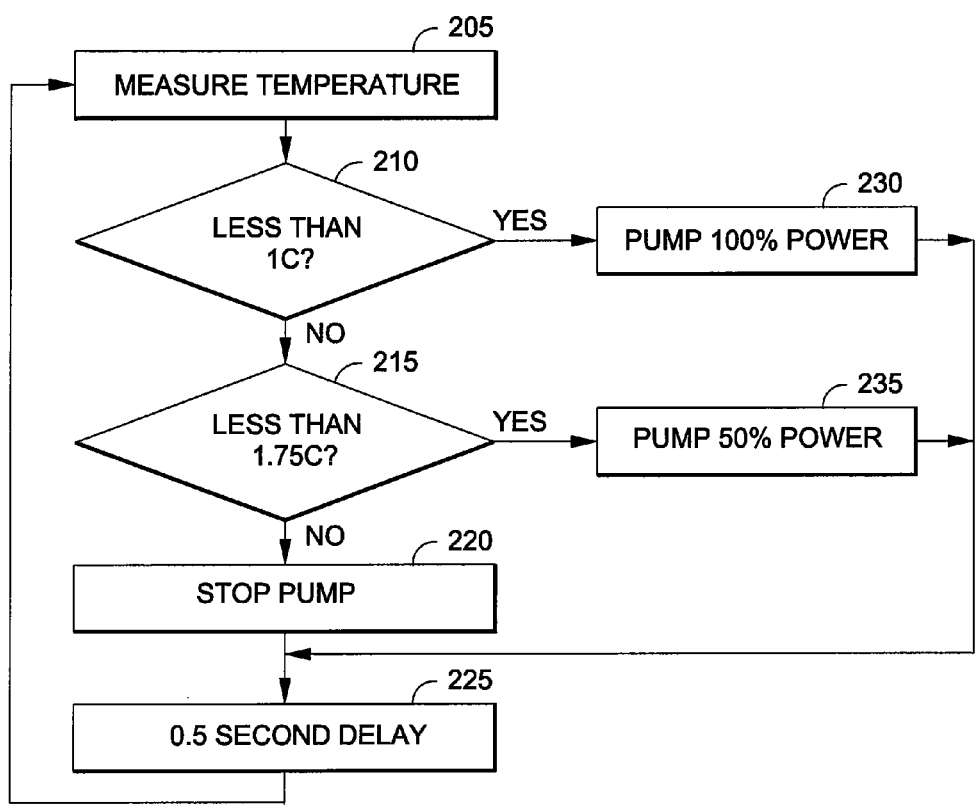
FIG. 2 illustrates a flow chart representing operation of an implantable pumping system according to an embodiment of the present invention.

In an embodiment, and with reference to FIG. 2, the system 100 is configured to measure the temperature of the system 100 at discrete intervals. At step 205, the temperature of the system 100 is measured. If the temperature change is less than a certain threshold at step 210, for example, less than 1 degree Celsius above an operational temperature parameter, then the pump 130 is set to 100% power at step 230. In various embodiments, the operational temperature of the system 100 may be determined by the steady state temperature of the pump 130 when the pump 130 has been at rest for a certain period of time. In other embodiments, the operational temperature of the pump 130 may be calibrated prior to and/or after implantation of the system 100. Other temperature sensors associated with other aspects of the system 100 may also be utilized to determine the operational temperature of the system 100.

For example, temperature sensors associated with the pump, an enclosure for the pumping system, a micro controller, and/or a radio transmitter may be used to measure the temperature of these and other components. The measured temperature of these components may be utilized to infer a temperature about the enclosure for the pumping system and/or about other aspects of the pumping system. In an embodiment, knowing and/or inferring the temperature of the enclosure facilitates determining whether or not the system is operating within acceptable parameters.

With continued reference to FIG. 2, if the temperature change measured at step 205 is greater than 1 degree Celsius but less than 1.75 degrees Celsius at step 215, then the pump 130 is set to 50% power at step 235. If the temperature change is greater than 1.75 degrees Celsius, then the pump 130 is stopped at step 220, to allow the temperature of the pump 130 to return to a desired level. A delay may then be introduced into the process flow, for example, a delay of 0.5 seconds at step 225, and the process is then repeated starting with measuring the temperature at step 205. In an embodiment, a desired value of the temperature change is between approximately −2 and approximately +2 degrees Celsius. Furthermore, in an embodiment, the measurements may be periodically repeated at an interval of between approximately 0.1 seconds and approximately 10 minutes. It should be understood that the numbers given in this illustration are simply example numbers according to an embodiment, and different temperatures and times may be utilized in accordance with various system parameters in various embodiments of the present invention. Further, other parameters such as pressure and/or flow rate may be manipulated in a similar manner.

In accordance with various embodiments, temperature sensors may exist in connection with various components of the system 100, and these temperature sensors may be utilized to measure the temperature change of the system 100. For example, temperature sensors in a micro controller, a radio, a pressure sensor, and other components may be utilized to determine the temperature change of the system 100. Because these sensors may be utilized for other functionality of the system 100 and/or they may be integral to these existing components, their use may not increase the volume needed for the system 100. In various embodiments, these sensors may be correlated and characterized to reflect the surface temperature of the enclosure for the system 100.

In a further embodiment, a separate temperature sensor may be located at the hottest part of the enclosure for the system 100. Such a temperature sensor is advantageous because it directly monitors the temperature of interest and may be able to more accurately facilitate control and operation of the system 100. Various combinations of sensors may be utilized in accordance with embodiments of the present invention. These sensors may measure temperature, flow rate, pressure, and/or other variables that indicate the temperature and/or other parameters of the system 100.

In conclusion, combining the various aspects of flow, pressure, and/or temperature monitoring to provide a range of pump performance, in accordance with various embodiments of the present invention, results in the system 100 meeting regulatory temperature requirements while maintaining control locally in the system. Such results may be accomplished by indirect and/or direct monitoring of the temperature within the system 100 using pump flow rate, pressure, and/or temperature in order to control the temperature of the system 100. Localizing the control of the system 100 is advantageous because it simplifies control of the system 100. Further, intelligent monitoring and control provides advantages over methods that indiscriminately switch the pump on and off without monitoring temperature or other parameters. For example, systems according to embodiments of the present invention provide more efficient pumping operation due in part to the monitoring and control of the pumping parameters disclosed herein.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for monitoring a parameter of an implantable pumping system for an implantable gastric banding system, the method comprising:
    measuring a temperature associated with the implantable pumping system;
    determining a temperature difference between the measured temperature and a predefined operational temperature, wherein the temperature difference is associated with power consumed by a pump at a set frequency and voltage;
    comparing the temperature difference to a predetermined difference that is between approximately −2 degrees Celsius and approximately +2 degrees Celsius from the predefined operational temperature; and
    when the temperature difference is between approximately −2 degrees Celsius and approximately +2 degrees Celsius from the predefined operational temperature, setting frequency and voltage of the power consumed by the pump as a function of the determined temperature difference so that the power consumed by the pump is up to a maximum power level.

2. A method for monitoring a parameter of an implantable pumping system for an implantable gastric banding system, the method comprising:

setting a frequency and voltage so that a pump operates at a maximum power level;

periodically measuring the parameter of the implantable pumping system, wherein the parameter is associated with power consumed by the pump;

comparing the measured parameter to a predetermined operational threshold;

when the measured parameter is above the predetermined operational threshold, adjusting one or both of the set frequency and voltage to reduce the power consumed by the pump;

turning the pump off when the measured parameter is above a predetermined maximum threshold, which is greater than the predetermined operational threshold; and after turning the pump off, when the measured parameter decreases below the predetermined maximum threshold, turning the pump on and re-setting the frequency and voltage so that the pump operates at the maximum power level.

3. A method for monitoring an implantable pumping system for an implantable gastric banding system, the method comprising:

measuring a parameter of the implantable pumping system, wherein the parameter is associated with power consumed by a pump of the pumping system when the pump is operating;

comparing the parameter to an operational range of values, and wherein when the measured parameter is within the operational range of values, comparing the measured parameter to predefined discrete intervals within the operational range of values;

turning a pump of the pumping system off when the measured parameter transitions from being within the operational range of values to being outside the operational range of values and turning the pump on when the measured parameter transitions from being outside the operational range of values to being within the operational range of values; and when the measured parameter is within the range of values, adjusting at least one of a frequency or voltage of the power consumed by the pump as a function of the respective discrete interval in which the measured parameter falls, wherein:

the frequency and/or voltage are adjusted so that the pump operates at a maximum power level when the measured parameter falls within a first discrete interval and are adjusted so that the pump operates at less than the maximum power level when the measured parameter falls within a second discrete interval.

* * * * *